US011795122B2

(12) United States Patent
Aguirrezabal et al.

(10) Patent No.: US 11,795,122 B2
(45) Date of Patent: Oct. 24, 2023

(54) REACTION PROCESS INVOLVING CAPILLARY CONDENSATION WITHIN A MICROPOROUS CATALYST

(71) Applicants: Research Triangle Institute, Research Triangle Park, NC (US); University of the Basque Country, Lejona (ES)

(72) Inventors: Iker Aguirrezabal, Research Triangle Park, NC (US); Ignacio Luz Minguez, Research Triangle Park, NC (US); Mustapha Soukri, Research Triangle Park, NC (US); Marty Lail, Research Triangle Park, NC (US); Pedro Luis Arias, Research Triangle Park, NC (US)

(73) Assignees: RESEARCH TRIANGLE INSTITUTE, Research Triangle Park, NC (US); UNIVERSITY OF THE BASQUE COUNTRY, Lejona (ES)

( * ) Notice: Subject to any disclaimer, the term of this patent is extended or adjusted under 35 U.S.C. 154(b) by 338 days.

(21) Appl. No.: 17/262,490

(22) PCT Filed: Jul. 17, 2019

(86) PCT No.: PCT/US2019/042118
§ 371 (c)(1),
(2) Date: Jan. 22, 2021

(87) PCT Pub. No.: WO2020/023256
PCT Pub. Date: Jan. 30, 2020

(65) Prior Publication Data
US 2021/0309588 A1    Oct. 7, 2021

Related U.S. Application Data

(60) Provisional application No. 62/703,684, filed on Jul. 26, 2018.

(51) Int. Cl.
C07C 2/32        (2006.01)
B01J 31/16       (2006.01)
B01J 35/10       (2006.01)

(52) U.S. Cl.
CPC ............ *C07C 2/32* (2013.01); *B01J 31/1691* (2013.01); *B01J 35/1057* (2013.01); *B01J 2231/12* (2013.01); *B01J 2531/821* (2013.01); *C07C 2523/46* (2013.01); *C07C 2531/22* (2013.01)

(58) Field of Classification Search
CPC ... C07C 2/32; C07C 2523/46; C07C 2531/22; B01J 31/1691; B01J 35/1057;
(Continued)

(56) References Cited

U.S. PATENT DOCUMENTS 8,865,266 B2 * 10/2014 Ahn .................... B05D 7/52
                                                    427/270
9,045,387 B2 *  6/2015 Yaghi .................. C07C 209/68
(Continued)

FOREIGN PATENT DOCUMENTS

EP    0256707 B1    11/1990
WO    2017210874 A1  12/2017
WO    2018031733 A1   2/2018

OTHER PUBLICATIONS

Agirrezabal-Telleria et al. ("Stabilization of active, selective, and regenerable Ni-based dimerization catalysts by condensation of ethene withinordered mesopores", Journal of Catalysis 352 (2017) 505-514). (Year: 2017).*
(Continued)

*Primary Examiner* — Ali Z Fadhel
(74) *Attorney, Agent, or Firm* — NK Patent Law

(57) ABSTRACT

Described herein is a catalytic reaction process including introducing one or more gas-phase reactants into a reactor comprising a microporous catalyst having a pore size less than or equal to 2 nm and adjusting the temperature and/or
(Continued)

the pressure of the reactor such that one or more of the gas-phase reactants condense within the micropores of the catalyst thereby causing the catalytic reaction to take place in a liquid phase. Additionally, a process for engineering defects on a carboxylate-based metal organic framework (MOF) catalyst is described. The process includes providing a carboxylate-based MOF catalyst; and heating the carboxylate-based MOF catalyst in an inert gas atmosphere at temperatures between about 150° C. and about 900° C.

20 Claims, 5 Drawing Sheets

(58) Field of Classification Search
CPC .............. B01J 2231/12; B01J 2531/821; B01J 29/035; B01J 31/2239; B01J 2231/20; B01J 2531/847
See application file for complete search history.

(56) References Cited

U.S. PATENT DOCUMENTS

| | | | |
|---|---|---|---|
| 2010/0186588 A1* | 7/2010 | Yaghi | ...................... C07F 3/003 546/10 |
| 2013/0296162 A1* | 11/2013 | Wright | .................. C07F 15/045 210/660 |
| 2017/0173518 A1* | 6/2017 | Chen | ...................... B01D 53/62 |
| 2018/0043330 A1 | 2/2018 | Friscic et al. | |
| 2020/0114189 A1* | 4/2020 | Ryu | ......................... A62D 3/34 |

OTHER PUBLICATIONS

ISA/US; International Search Report and Written Opinion for International Patent Application No. PCT/US2019/042118 dated Nov. 21, 2019, 16 pages.
Agirrezabal-Telleria, Iker., et al., "Stabilization of active, selective, and regenerable Ni-based dimerization catalysts by condensation of ethene withinordered mesopores", Elsevier, Journal of Catalysis, vol. 352, 2017, 10 pages.
Madrahimov, Sherzod, et al., "Gas-Phase Dimerization of Ethylene under Mild Conditions Catalyzed by MOF Materials Containing (bpy)Nill Complexes", ACS Catalysis, vol. 5, 2015, 6 pages.
Andrei, Radu Dorin, et al., "Heterogeneous oligomerization of ethylene over highly active and stable Ni-AISBA-15 mesoporous catalysts", Elsevier, Journal of Catalysis, vol. 323, 2015, 9 pages.
WIPO; International Preliminary Report on Patentability for International Patent Application No. PCT/US19/42118 dated Feb. 4, 2021, 12 pages.

* cited by examiner

REACTION PROCESS INVOLVING CAPILLARY CONDENSATION WITHIN A MICROPOROUS CATALYST

CROSS-REFERENCE TO RELATED APPLICATIONS

This application is a U.S. National Stage application of International Patent Application No. PCT/US19/42118, filed on Jul. 17, 2019, which claims the benefit of U.S. Provisional Patent Application No. 62/703,684, filed on Jul. 26, 2018, the entire contents of which are incorporated herein by reference.

STATEMENT REGARDING FEDERALLY SPONSORED RESEARCH OR DEVELOPMENT

This invention was made with government support under DE-FE0026432 awarded by US Department of Energy. The government has certain rights in the invention.

FIELD

The present disclosure describes a catalytic reaction process involving capillary condensation of a gas-phase reactant within the pores of a microporous catalyst. Also described is a method for thermally engineering catalytically active sites on metal organic frameworks.

BACKGROUND

Conventional catalysis reactions are performed using gas-reactants (in fixed beds, slurries or bubbled in solvents) or liquid-reactants (under pressurized conditions and/or using additional solvents). Generally, solid-catalysts are used with gas-reactants at relatively high temperatures because gas phase reactants typically provide benefits in terms of enhanced reactivity and diffusion. Generally, liquid-reactants provide enhanced solvation effects and selectivity. It is desirable to have a process that provides the benefits of both gas phase reactants and liquid phase reactants.

Both liquid phase and gas phase catalyst-enabled reactions are used to convert light alkenes into their associated dimers. With regard to liquid phase reactions, solvent-enabled C—C coupling of alkenes is ubiquitous in homogeneous catalysis. The liquid phase reactions have stable rates with liquids interacting with kinetically-relevant intermediates. Transition-metals (Ti, Ni, Cr) within organometallic liquids or heterogeneous supports selectively convert light alkenes ($C_2$-$C_4$) into highly industrially-relevant dimers. With regard to gas phase reactions, solid-catalysts experience fast deactivation rates due to irreversible deposition of heavy oligomers at the higher reaction temperatures than the ones used for liquid reaction systems.

It has been shown that catalyst deactivation rates can be lowered for gas phase ethylene reactions if the reactants are condensed in mesoporous catalysts having pores around 2 nm or greater. See, *Stabilization of active, selective, and regenerable Ni-based dimerization catalysts by condensation of ethylene within ordered mesopores*, Journal of Catalysis 352 (2017) 505-514. However, the mesopore catalysts required high-pressures and sub-ambient temperatures to maintain the high-volatility reactants as intrapore liquids. It would be advantageous to be able to perform these types of capillary condensation reactions at relatively lower pressures and industrially feasible temperatures.

Moreover, most homogeneous catalysts or heterogeneous MOF catalysts depend on co-catalysts for converting light alkenes to their associated dimers because the co-catalysts allow the formation of active ethyl-intermediate species. The dependence on co-catalysts minimizes the practical use of MOF catalysts (and other homogenous catalysts) in alkene oligomerization reactions. It is desirable to provide a MOF catalyst that does not need an activator or a solvent for alkene oligomerization reactions.

SUMMARY OF THE DISCLOSURE

A first aspect of the invention includes a catalytic reaction process. The catalytic reaction process includes providing a reactor including a microporous catalyst having a defined pore size distribution with a pore diameter ≤2 nm, thereby allowing a controlled pore-filling. The catalytic reaction process also includes introducing one or more gas-phase reactants into the reactor. The catalytic reaction process also includes adjusting the temperature and/or the pressure of the reactor such that one or more of the gas-phase reactants, products or mixed reactant-products condense to form a liquid phase fraction within the micropores of the catalyst. The liquid phase fraction in the micropores can be controlled to achieve a mixed liquid/gas phase within the micropores such that the catalytic reaction takes place in a liquid phase.

Implementations of the first aspect may include one or more of the following features. The process where the reactor operates at a temperature in a range of about −30° C. to about 200° C. and at a pressure in a range of about 0.1 MPa and about 10 MPa. The process further includes, prior to introducing the one or more gas-phase reactants to the reactor, heating the microporous catalyst in an inert gas atmosphere at a temperature between about 150° C. and about 900° C., where the microporous catalyst includes a carboxylate-based MOF catalyst. The process where the catalytic reaction includes C—C coupling reactions or chain-growth reactions, ethylene epoxidation, ethylene hydrochlorination, CO hydrogenation reactions, or $CO_2$ hydrogenation reactions. The process where the microporous catalyst includes a metal organic framework (MOF), zeolites, zeotypes, covalent organic frameworks (COF), porous organic polymers, porous molecular solids, porous carbons, or other porous catalysts containing silica, organo-silica, silicoaluminate, aluminophosphate, titania, zirconia, and/or ceria.

A second aspect of the invention includes a process for converting ethylene into its associated oligomer. The process includes providing a reactor including a microporous catalyst having a pore size ≤2 nm, where the reactor operates at a temperature between about −30° C. and about 200° C. and at a pressure between about 0.1 MPa and about 10 MPa. The process also includes introducing a gas-phase ethylene reactant into the reactor. The process also includes adjusting the temperature and/or the pressure of the reactor such that at least a portion of the gas-phase ethylene reactant condenses within the micropores of the catalyst thereby causing the catalytic reaction to take place in a liquid phase.

A third aspect of the invention includes a process for converting a C2-C4 alkene into its associated oligomer. The process includes providing a reactor including a microporous catalyst having a pore size ≤2 nm, where the reactor operates at a temperature between about −30° C. and about 200° C. and at a pressure between about 0.1 MPa and about 10 MPa. The process also includes introducing one or more gas-phase C2-C4 alkene reactants into the reactor. The process also includes adjusting the temperature and/or the pressure of the reactor such that at least a portion of one or more gas-phase C2-C4 alkene reactants condenses within the micropores of the catalyst thereby causing the catalytic reaction to take place in a liquid phase.

A fourth aspect of the invention includes a process for generating catalytically active sites on a carboxylate-based metal organic framework (MOF) catalyst. The process includes providing a carboxylate-based MOF catalyst. The process also includes heating the carboxylate-based MOF catalyst in an inert gas atmosphere at a temperature between about 150° C. and about 900° C.

A fifth aspect of the invention includes a process for engineering defects on a carboxylate-based metal organic framework (MOF) catalyst. The process includes providing a carboxylate-based MOF catalyst. The process also includes heating the carboxylate-based MOF catalyst in an inert gas atmosphere at temperatures between about 150° C. and about 900° C.

DETAILED DESCRIPTION

Figure 1A:
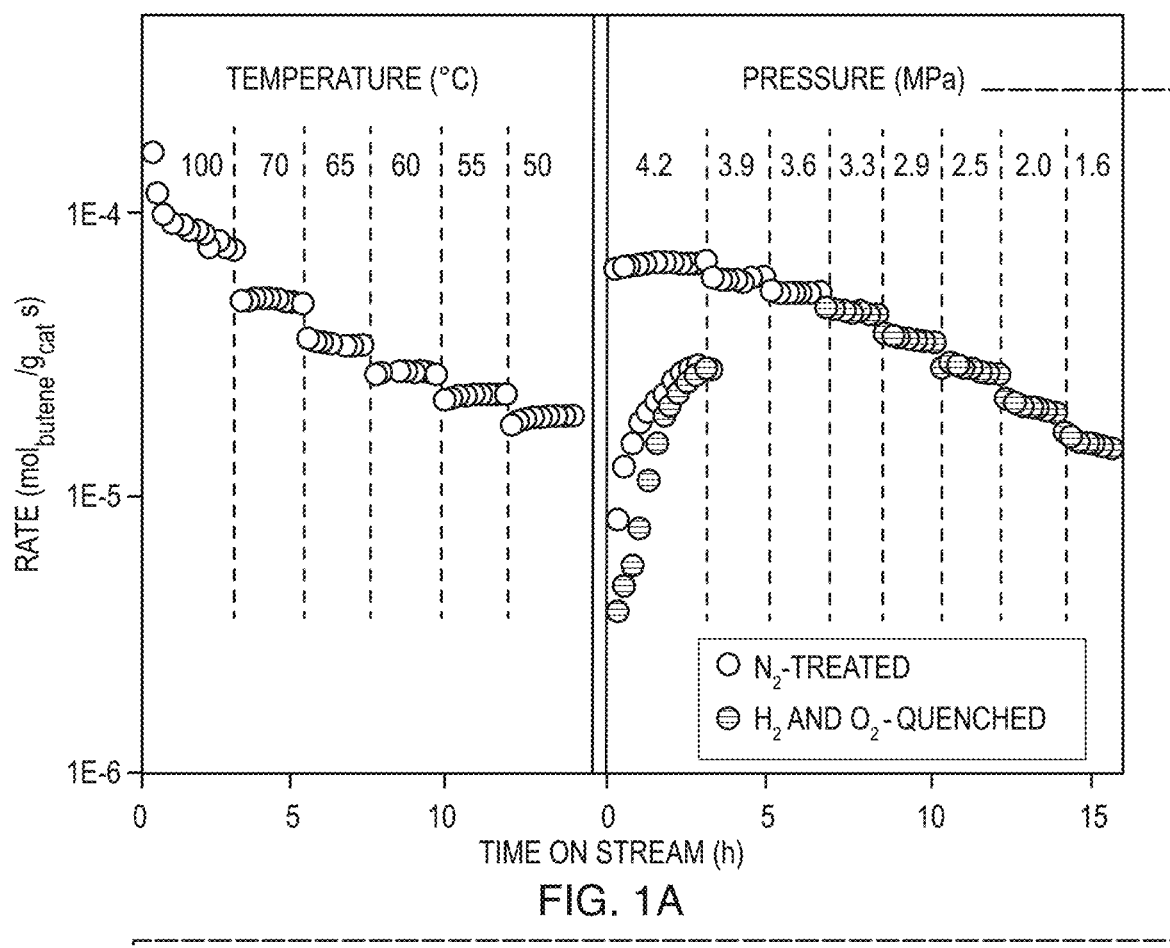
FIG. 1A is graph showing butene formation rates as a function of temperature at 4.2 MPa ethylene (left) and as a function of ethylene pressure at 50° C. (right) as described in Example 1.

Described herein is a catalytic reaction process involving capillary condensation of a gas-phase reactant within the pores of a microporous catalyst. The catalytic reaction process includes providing a reactor comprising a microporous catalyst having a pore size less than or equal to 2 nm, wherein the reactor operates at a temperature and a pressure. Reactor operating temperature and pressure can be selected and optimized based on a number of considerations. A non-exclusive list of exemplary considerations includes reactant composition, catalyst composition and structure, reactor temperature and pressure limitations, and operating temperature and pressure of associated processes. One or more gas-phase reactants are introduced into the reactor, catalysts pore size, and temperature and/or the pressure of the reactor can be adjusted such that at least one or more of the gas-phase reactants condenses within the micropores of the catalyst thereby causing the catalytic reaction to take place in a liquid phase. Operating the reactor in such a way as to condense at least one or more of the gas-phase reactants into the liquid phase in the micropores of the catalyst provides advantages that will be discussed in greater detail below.

In an embodiment, the catalytic reaction process comprises providing a reactor comprising a microporous catalyst having a defined pore size distribution with a pore diameter ≤2 nm, thereby allowing a controlled pore-filling. One or more gas-phase reactants are introduced into the reactor. The temperature and/or the pressure of the reactor are adjusted such that one or more of the gas-phase reactants, products or mixed reactant-products condenses to form a liquid phase fraction within the micropores of the catalyst. The liquid phase fraction in the micropores is controlled to achieve a mixed liquid/gas phase within the micropores such that the catalytic reaction takes place in a liquid phase. The temperature and pressure can be adjusted such that that only a liquid phase is present within the micropores.

As mentioned above, the operating temperature and pressure can be determined based on various operating considerations. Generally, the reactor will be operated in a temperature range of about −30° C. to about 200° C. and at a pressure range of about 0.1 MPa and about 10 MPa. Higher or lower temperatures and pressures may be used as appropriate. In embodiments, the reactor may be operated at a temperature in a range of about 0° C. to about 150° C. For example, the reactor may be operated at about 0° C., 20° C., 30° C., 40° C., 50° C., 60° C., 70° C., 80° C., 90° C., 100° C., 110° C., or 120° C. In embodiments, the reactor may be operated at a pressure in a range of about 0.5 MPa to about 8 MPa. For example, the reactor may be operated at about 1.0 MPa, 1.5 MPa, 2.0 MPa, 2.5 MPa, 3.0 MPa, 3.5 MPa, 4.0 MPa, 4.5 MPa, 5.0 MPa, 5.5 MPa, 6.0 MPa, 6.5 MPa, 7.0 MPa, 7.5 MPa, or 8.0 MPa.

These reactions can be carried out in reactors containing porous catalysts in various forms, such as fixed-bed or fluidized flow reactors, or would also be applicable to batch reactors allowing the intrapore condensation of reactants or products In the process described herein, gas-reactants are at least partially condensed into liquid-phase reactants within microporous materials (under certain conditions of pressure and temperature) having catalytically active sites disposed throughout the micropores. The capillary catalytic condensation process provides the kinetic benefits of both gas- and liquid-phase reaction conditions. Exemplary benefits include, but are not limited to: 1) enhanced reactivity and diffusion (gas-phase), 2) improved heat dissipation in exothermic conditions compared to conventional gas-phase conditions, and 3) stabilization of specific reaction surface intermediates that directly affect catalyst deactivation (liquid-phase). Exemplary reaction surface intermediates may include desorption intermediates of bound species. Without being bound by theory, it is believed that the capillary condensation of reactants enables stabilization of reaction surface intermediates that directly affect catalyst deactivation, providing long-term catalyst stability within the microporous catalysts.

Microporous materials offer unique tunability in terms of pore architecture and nature of catalytically active sites, which enables tailoring active and stable microporous catalyst for reactions performed under a capillary-condensation regime. Microporous catalysts may comprise exemplary microporous materials, including, but not limited to, metal organic frameworks (MOFs), zeolites, zeotypes, covalent organic frameworks (COF), porous organic polymers, porous molecular solids, porous carbons, as well as other porous catalysts containing silica, organosilica, silicoaluminate, aluminophosphate, titania, zirconia, and/or ceria. As used herein, a metal organic framework (MOF) may refer to compounds consisting of metal ions or clusters coordinated to organic ligands to form one-, two- or three-dimensional structures, with the special feature of porosity. More formally, a metal organic framework is a coordination network with organic ligands containing potential voids. In a preferred embodiment, the nano-crystalline MOF has a percent porosity of greater than 10%, preferably greater than 20%, preferably greater than 25%, preferably greater than 30%, preferably greater than 35%, preferably greater than 40%. MOFs are composed of two major components: a metal ion or cluster of metal ions and an organic molecule often termed a linker. The organic units are typically mono-, di-, tri-, or tetravalent ligands. The choice of metal and linker will dictate the structure and hence properties of the MOF. For example, the metal's coordination preference influences the size and shape of pores by dictating how many ligands can bind to the metal and in which orientation. The metal ion or cluster of metal ions associated with the MOF catalyst used herein may include metals from alkali metals, alkali earth metals, transition metals, rare earth metals or other metals. For example, the metal ion or cluster of metal ions may include, without limitation, Mg, V, Cr, Mo, Zr, Hf, La, Zr, Mn, Fe, Co, Cu, Ni, Zn, Ru, Al, Ga, or mixtures thereof. In a preferred embodiment, the associated metal ion(s) comprise Ru or Ni. The organic ligand associated with the MOF catalyst may include organic ligands comprising polycarboxylate ligands, azaheterocyclic ligands, or derivatives thereof. For example, the organic ligand may include, without limitation, terephthalate, benzene-1,3,5-tricarboxylate, 2,5-dioxibenzene dicarboxylate, biphenyl-4,4'-dicarboxylate or derivatives thereof.

In an exemplary embodiment, the linker of the MOF catalyst comprises a carboxylate. In preferred embodiments, the MOF structures used herein are microporous, having average pore sizes ranging from 0 nm to 2 nm.

Many catalysts depend on co-catalysts for reactivity, which minimizes their potential practical use in reactions (for example, alkene oligomerization reactions). For example, homogeneous and heterogeneous catalysts, including MOF catalysts, often require large amounts of activators (up to 500 equivalents per active metal) for assuring the formation and stabilization of alkyl-metal active species during ethylene dimerization. In the process described herein, an activator-free and solvent-free MOF catalyst can be used to provide good dimerization reactivity and good stability to products via capillary condensation at relatively mild temperatures.

One or more of the gas-phase reactants may be partially condensed or completely condensed within the micropores of the catalyst. For example, the portion of condensed gas-phase reactants may be 10 wt %, 20 wt %, 30 wt %, 40 wt %, 50 wt %, 60 wt %, 70 wt %, 80 wt %, 90 wt %, or 100 wt %. In preferred embodiments, the gas-phase reactants are completely or 100% condensed.

It is conventionally known that catalytically active open metal sites (i.e., defects) can be engineered on Ru-based MOF catalysts via controlled in-synthesis incorporation of coordinatively deficient ligands (up to 30% in the MOF structure). Catalysts with engineered defects have demonstrated an enhanced reactivity for several reactions (e.g., alkene hydrogenation) while maintaining structural stability. Thus, it is known that engineered defects can be beneficial for catalytic purposes.

Advantageously, it has surprisingly been found that thermal activation or treatment under an inert gas can produce carboxylate-based MOF catalysts having a high concentration of catalytically active metal-hydride sites. Thermal treatment of previously synthesized MOF catalysts provides a general, elegant and efficient method for engineering catalytically active sites compared to in-synthesis incorporation of coordinatively deficient ligands for the same purpose, which was previously used.

Thus, also described herein is a process for generating catalytically active sites on a carboxylate-based metal organic framework (MOF) catalyst. The process includes providing a carboxylate-based MOF catalyst; and heating the carboxylate-based MOF catalyst in an inert gas atmosphere at a temperature between about 150° C. and about 900° C. The MOF catalyst may be microporous or mesoporous. For example, the MOF catalyst may be mesoporous, having pore sizes with an average diameterin the range of 2-50 nm, preferably 4-45 nm, preferably 6-40 nm. The MOF catalyst may be microporous, having pore sizes with an average diameter in the range of 0-5.0 nm, preferably 1.0-3.0 nm, preferably 1.0-2.0 nm.

The MOF catalyst can be heated at a temperature range between about 150° C. and about 900° C. For example, in embodiments, the temperature range may be about 100-700° C., about 150-600° C., about 200-500° C., about 200-400° C., 200-300° C. or about 300-400° C. In an exemplary embodiment, the MOF catalyst may be heated for a time between about 30 minutes and about 2 hours. The concentration of generated defects can be selected based on the end use of the catalyst. For example, the concentration may be between about 2% and about 50%. In embodiments, the concentration of defects may be between about 2% and about 35%, between about 2% and about 30%, between about 2% and about 25%, between about 2% and about 20%, between about 5% and about 15%, or between about 7% and about 10%.

A carboxylate-based MOF catalyst that has thermally engineered defects can be used in the catalytic capillary condensation process described above. Thus, in embodiments, the capillary condensation process described herein also includes thermal treatment of the microporous catalyst prior to a gas-phase reactant being introduced to the reactor. The microporous catalyst can be heated in an inert gas atmosphere at a temperature between about 150° C. and about 900° C. In an exemplary embodiment, the microporous catalyst is a carboxylate-based MOF catalyst and the inert gas is $N_2$.

The microporous catalyst frameworks used in the capillary condensation process described above can be thermally treated to produce catalysts having catalytically active, selective and highly-stable open metal sites. Combining the two concepts can provide advantageous results.

In an exemplary embodiment of the capillary condensation catalytic reaction process, $C_2$-$C_4$ alkene can be converted into its associated oligomer. The process includes providing a reactor comprising a microporous catalyst having a pore size ≤2 nm, wherein the reactor operates at a temperature in a range of about 0° C. to about 200° C. and at a pressure in a range of about 0.1 MPa to about 10 MPa. The gas-phase $C_2$-$C_4$ alkene reactant is introduced into the reactor, and the temperature and/or the pressure of the reactor is adjusted such that at least a portion of the gas-phase $C_2$-$C_4$ alkene reactant condenses within the micropores of the catalyst thereby causing the catalytic reaction to take place in a liquid phase. In an embodiment, the $C_2$-$C_4$ alkene reactant comprises ethylene.

It is recognized by those of skill in the art that olefin-derived oligomers are a common catalyst deactivation source in the chemical industry. As described above, the catalytic capillary condensation process enables stabilization of reaction surface intermediates that lead to catalyst deactivation. Thus, the described method can provide long term stability within microporous catalysts.

EXAMPLES

Example 1

The following is an example of ethylene dimerization performed using the capillary condensation reaction method described herein at varying temperatures and pressures.

A Ru-containing MOF catalyst with an average pore size of 1.5 nm was first treated at 200° C. in $N_2$ (to remove labile adsorbates) and activated at 150° C. in $H_2$ to generate Ru-hydride species. The MOF catalyst contained 25% of defective ligand ($MOF_{L25}$).

Ethylene was introduced to the reactor for the ethylene dimerization reaction. To analyze the effect of temperature on the reaction, the reactor operating temperature was varied, with temperatures ranging from 50° C. to 100° C. Operating pressure was held at 4.2 MPa during the variable temperature period. To analyze the effect of pressure on the reaction, reactor operating pressures were varied. Pressures ranged from 1.6 MPa to 4.2 MPa. Operating temperature was held steady at 50° C. during the variable pressure period.

FIG. 1A provides a graph showing butene formation rates as a function of temperature and pressure. As shown in FIG. 1A, stable ethylene dimerization rates were achieved at temperatures below 60° C. (left side—pressure held at 4.2 MPa) or pressures above 3.3 MPa (right side—temperature held at 50° C.).

Figure 1B:
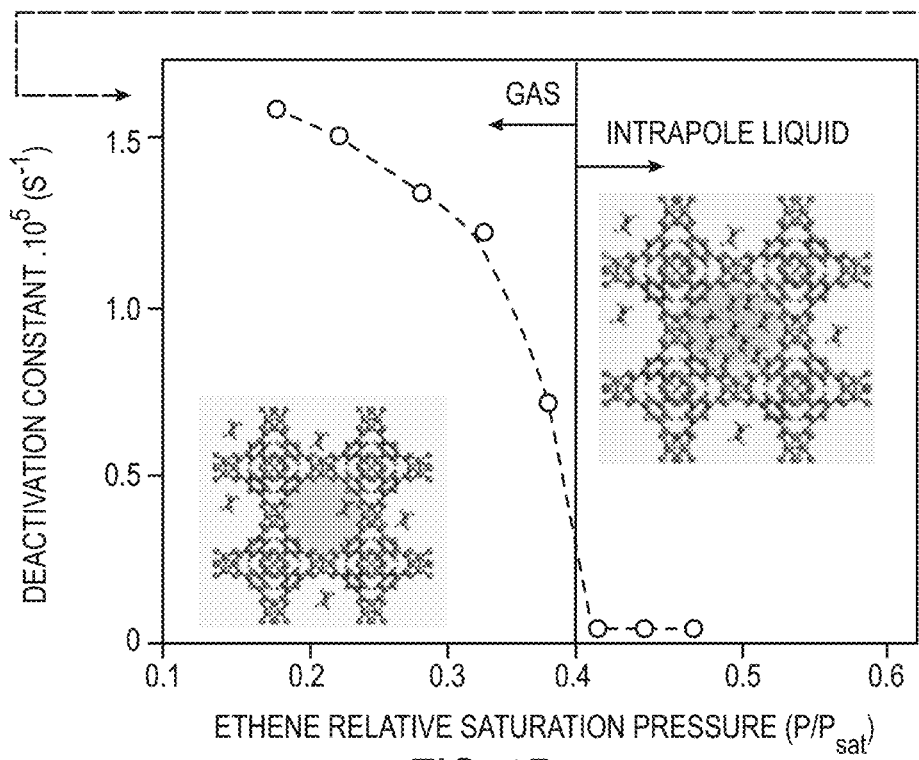
FIG. 1B is a graph showing first-order deactivation constants as a function of ethylene relative saturation pressure within $MOF_{L25}$ after a pretreatment in $H_2$ at 150° C. as described in Example 1.

The reaction conditions and the narrow pore structure (1.5 nm) suggest that active-site stabilization may be related to ethylene reactant condensation within the MOF micropores during the reaction. FIG. 1B provides a graph showing first order deactivation constants, derived from ethylene pressure changes (shown in FIG. 1A), as a function of ethylene relative saturation pressure within the MOF catalyst. Catalyst deactivation was undetectable at $P/P_{sat}$>0.4, whereas lower relative saturation pressures ($P/P_{sat}$) lead to a continuous increase in first-order deactivation constants as saturation pressures were decreased.

The decreasing rates-slopes as conversion decreased in FIG. 1A and the presence of an intrapore solvating environment suggests that ethylene-liquid interacts with bound alkene desorption intermediates before larger alkenes were formed.

Overall, the data in FIG. 1B show improved active Ru-hydride stabilization in MOFs under liquid-ethylene reactants and gas-phase precursors relative to reported MOF catalysts using activators and various liquid solvents.

Example 2

An exemplary process for using a thermal mechanism to engineer defects in MOF catalysts was performed. TGA and IR analyses coupled to MS were used to demonstrate the process.

Figure 2A:
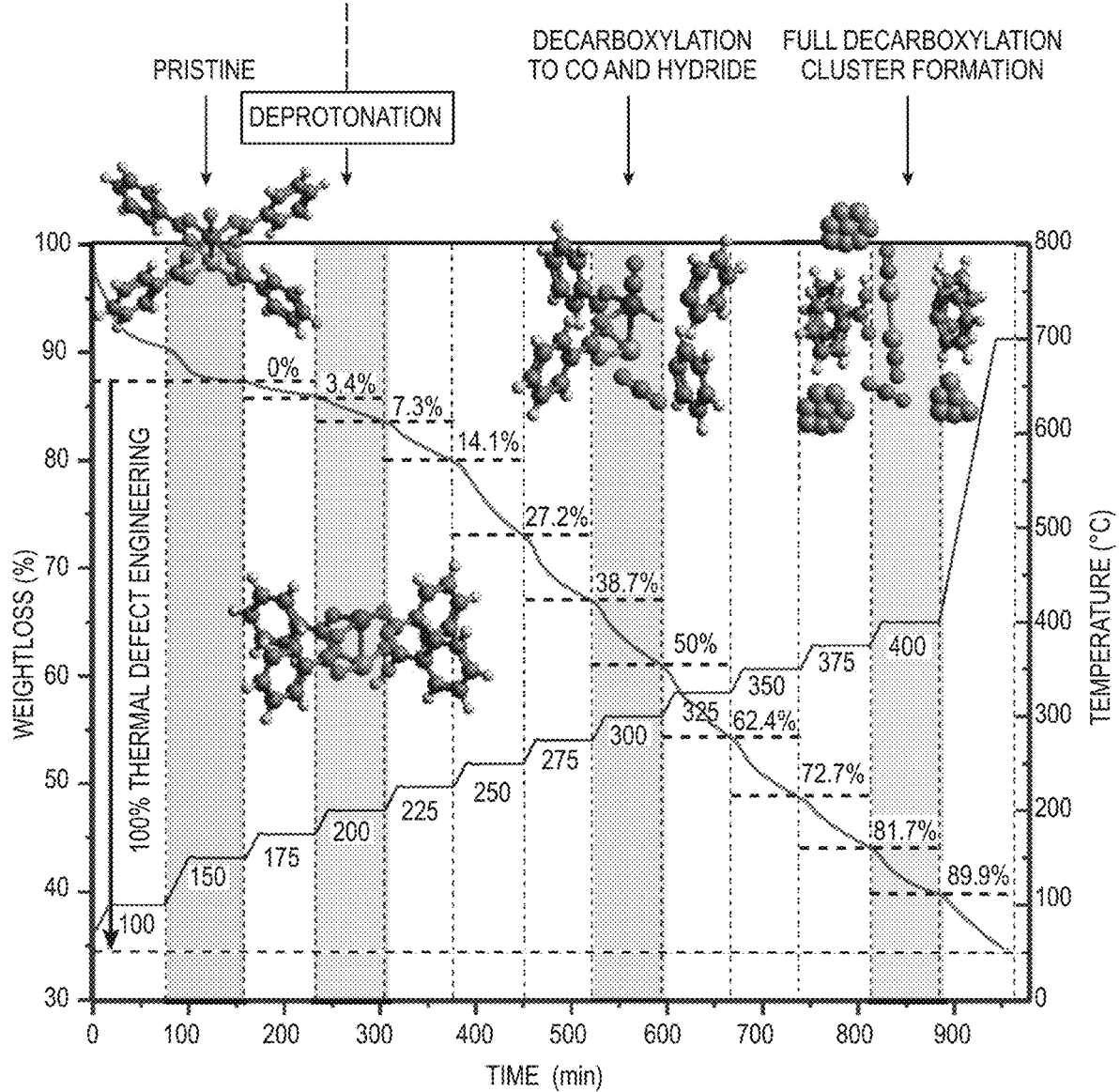
FIG. 2A is a graph showing thermo gravimetric analysis (TGA) of thermal-engineering defects in a $MOF_{L0}$ catalyst as described in Example 2.
Figure 2B:
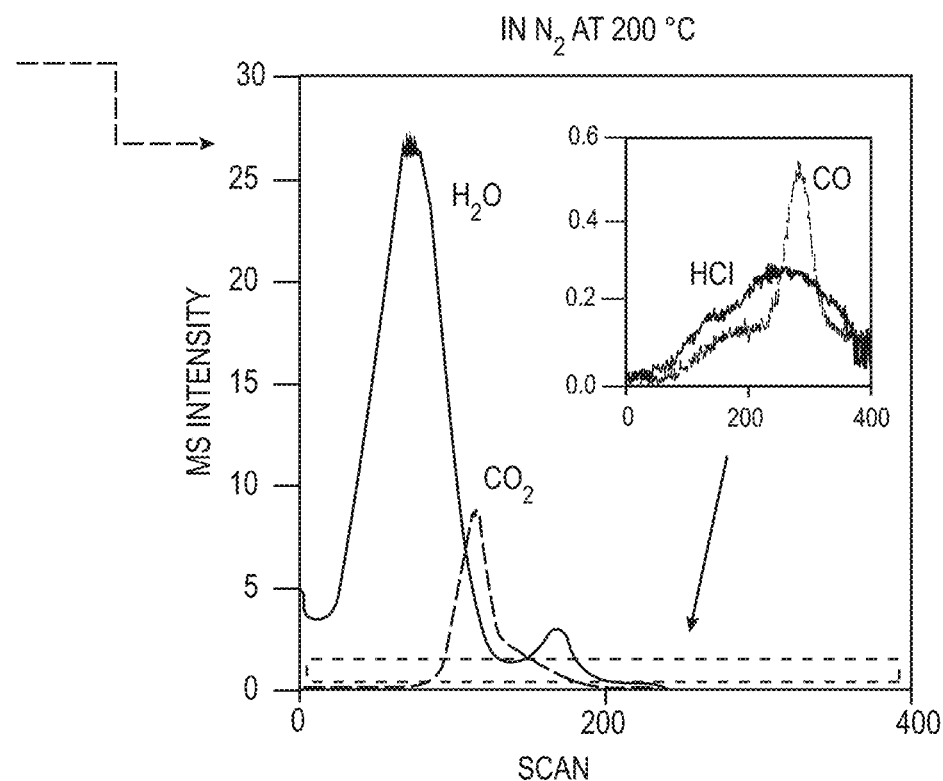
FIG. 2B is a graph showing detection of desorbed species from mass-spectrometer (MS) signal during Ar-treatment at 200° C. as described in Example 2.
Figure 2C:
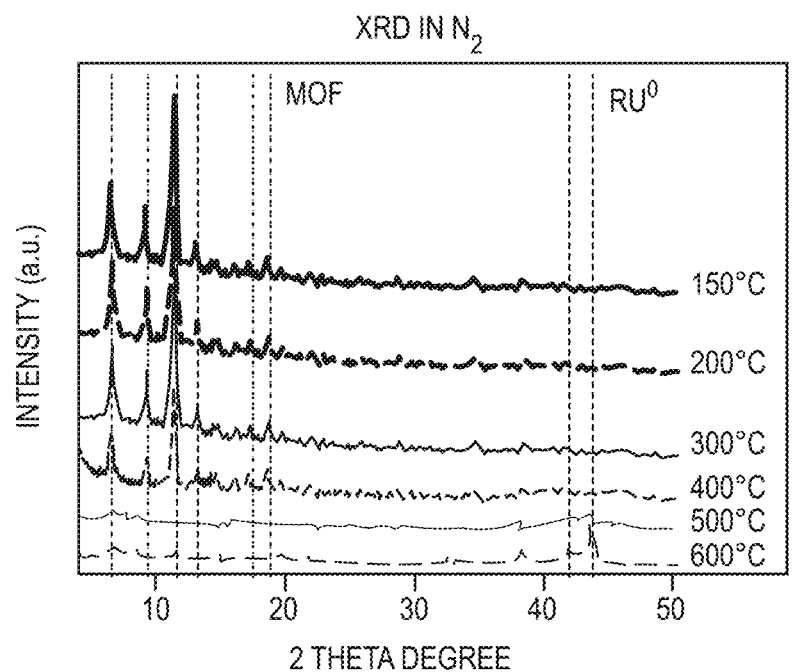
FIG. 2C is a graph showing XRD analyses after thermal-engineering defects in a $MOF_{L0}$ catalyst as described in Example 2.

A Ru carboxylate-based MOF catalyst with no surface defects was heated at increasing temperatures (from 0° C. to 700° C.) to determine the effects on the catalyst surface. FIGS. 2A, 2B, and 2C are charts showing various analyses performed during the staged heating process. FIG. 2A provides thermo gravimetric analysis (TGA) of thermal-engineering defects in the catalyst, which was originally defect free ($MOF_{L0}$). FIG. 2B provides a graph illustrating detection of desorbed species from mass-spectrometer (MS) signal during Ar-treatment at 200° C., and FIG. 2C provides XRD analyses after thermal-engineering of defects in the MOF catalyst.

An initial TGA-MS experiment suggested that a defect mechanism involving ligand decarboxylation. Further TGA analysis at increasing temperatures in $N_2$ (FIG. 2a) enabled the determination of the concentration of thermal-engineered defects for the MOF sample from the weight loss in the equilibrium (after 1-hour holding). The catalyst showed 100% defect content at a temperature of 700° C.

The testing also showed that 7.3% of defects can be engineered by thermal treatment in $N_2$ at 200° C. (FIG. 2a). This result shows that the MOF catalyst with thermal-engineered defects would be active for ethylene dimerization, unlike a counterpart $MOF_{L0}$ catalyst heat treated at 150° C. in $N_2$ (considered to contain 0% defects).

Figure 3A:
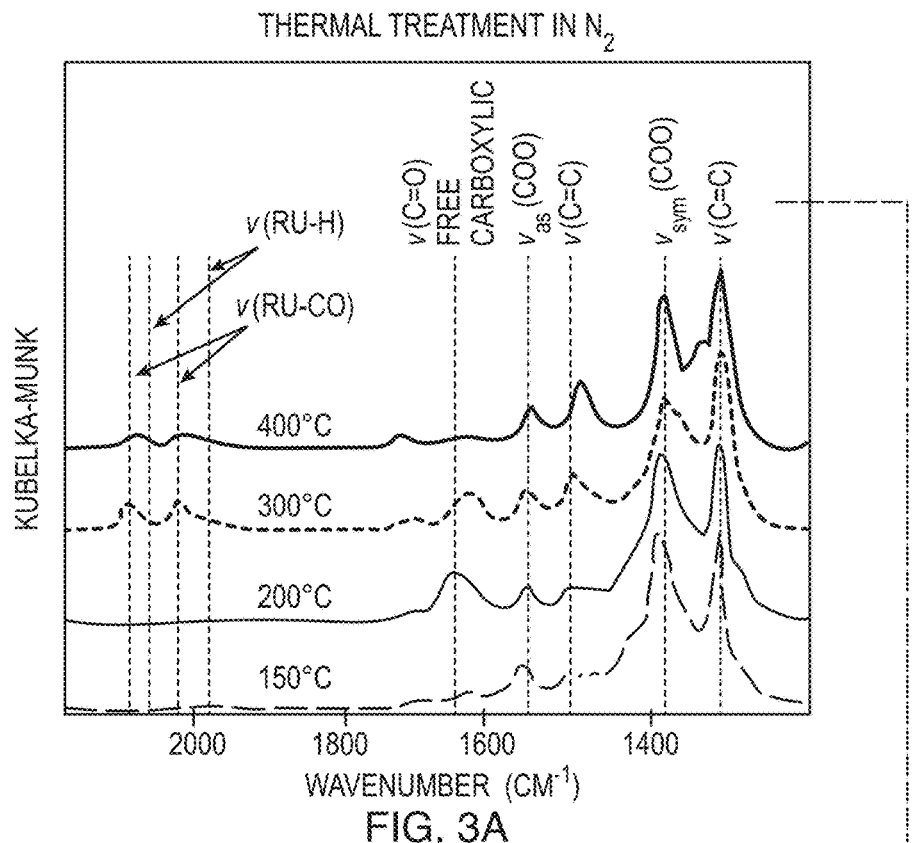
FIG. 3A is a graph showing DRIFT spectra of thermal-engineering of defects in $MOF_{L0}$ in $N_2$ as described in Example 2.
Figure 3B:
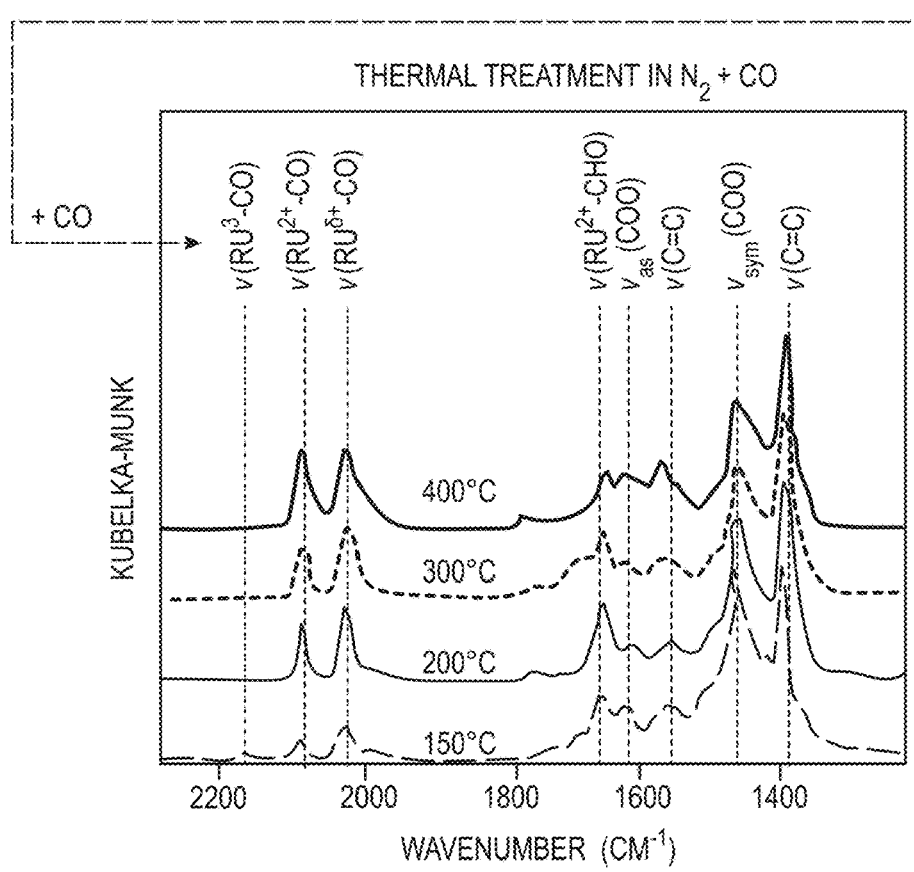
FIG. 3B is a graph showing DRIFT spectra of thermal-engineering of defects in $MOF_{L0}$ in $N_2$ and after CO adsorption at 30° C. as described in Example 2.

As can be seen in FIGS. 3A and 3B, the mechanism for such defect formation was also supported by IR data for MOF at increasing temperatures in $N_2$. FIGS. 3A and 3B are graphs providing DRIFT spectra of thermal-engineering of defects in MOF in $N_2$ (A) and after CO adsorption at 30° C. (B). An apparent carboxylate protonation occurring at 200° C., as a new vibrational band appeared at 1,698 $cm^{-1}$, attributed to stretching of carbonyl of free carboxylic acids [$v$(C=O)], suggests the partial reduction of at least one of the dimer Ru atoms to compensate the charge over the MOF node. The reduction of $Ru^{3+}$ observed at this temperature range can also be supported by two evidences: 1) the release of HCl identified by MS (FIG. 2B), and 2) the disappearance of the IR signal attributed to $Ru^{3+}$—CO species observed for the material at 150° C. (FIG. 3B). The experimental results show the excellent defect tunability provided by in-situ thermal engineering of MOF catalysts. This ability is advantageous in view of more limited in-synthesis ligand incorporation methods that have been used previously.

As observed in the IR spectra of MOF with thermal-engineered defects at 200-300° C. (FIGS. 3A and 3B), the progressive attenuation of signals for asymmetric stretching of carboxylates [$v_{sym}$(COO)] at 1,459 $cm^{-1}$, as well as the previous signal attributed to free carboxylic acids at 1,698 $cm^{-1}$ (as phenyl ring stretching signal at 1,384 $cm^{-1}$ [$v$(C=C)] remains constant), suggest that thermal activation above 200° C. occurs via cleavage of one of the carboxylates from the benzene tricarboxylate ligand to $CO_2$. This evidence is consistent with the considerable weightloss due to the release of large amount of $CO_2$ (50% of defects at 300° C., FIG. 2A). The appearance of vibrational bands between 2100-1900 $cm^{-1}$ (FIGS. 3A and 3B), attributed to CO and hydride adsorbed species on the Ru dimer at temperatures above 200° C., suggests their origin from the homolytic cleavage of carboxylates (see FIG. 3A).

In-situ XRD monitoring as a function of temperature on $MOF_{L0}$ (FIG. 2C) revealed the remarkable structural stability of the MOF crystalline structure up to 300° C. under $N_2$. Higher temperatures led to the appearance of a broad signal centered at 42 theta degrees that became even sharper diffraction peaks above 400° C., which is attributed to the aggregation of partially reduced Ru dimers into larger metallic Ru clusters, as also confirmed by XPS (This is accompanied by the evident signs of the MOF structure collapse due to the advanced degree of decarboxylation (up to 90%) and the attenuation of Ru—H and Ru—CO adsorbed species (FIG. 3A).

These results reveal an advantageous and straightforward route to create catalytically active sites from as-synthesized inactive MOFs. The thermal treatment method enables the direct utilization of MOF catalysts exhibiting thermal-generated Ru-hydride species for ethylene dimerization without requiring any $H_2$-activation, as demonstrated later.

Figure 4A:
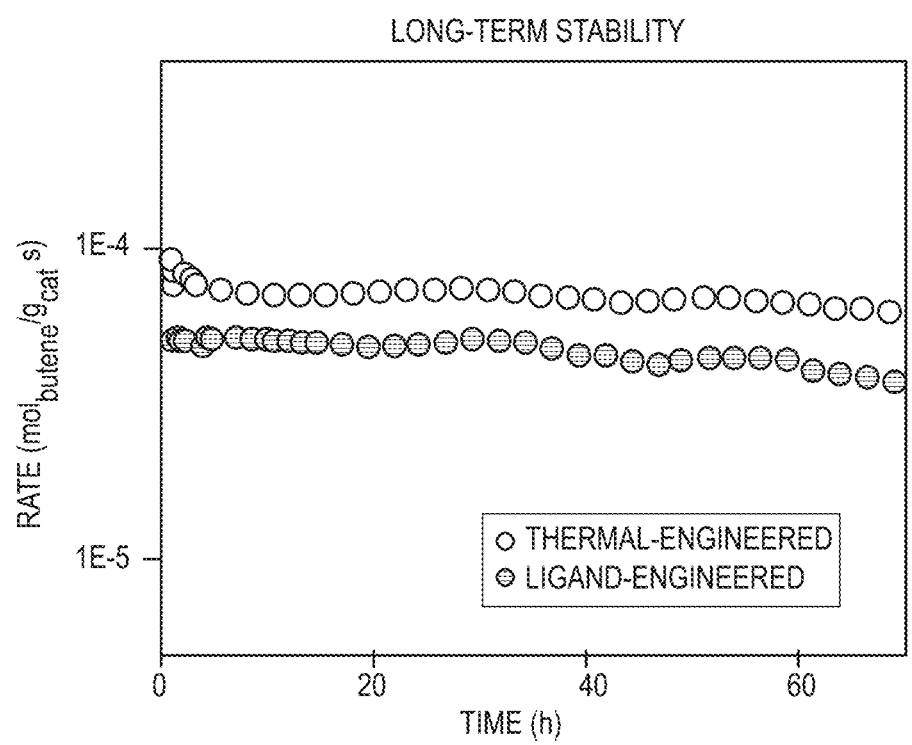
FIG. 4A is a graph showing the results of long-term dimerization reaction stability tests for ligand-defects versus thermal-engineered defects in MOFs at 50° C. and 4.2 MPa ethylene as described in Example 2.

FIG. 4A is a graph showing long-term stability dimerization rate data in the presence of intrapore liquid-ethylene for a Ru—H catalyst species formed via ligand ($H_2$-activated $MOF_{L10}$) and for a Ru—H catalyst species formed via thermal engineering of defects ($MOF_{L0}$ activated at 300° C. under $N_2$) at 50° C. and 4.2 MPa ethylene.

As shown in FIG. 4A, the Ru—H formation control and MOF structural stability of thermal-engineered defects seems to extrapolate to the long-term stability tests of these MOF catalysts. Such results indicated improved performance ability over currently available Ni-MOF catalysts during dimerization reactions, even in the presence of activators or liquid-solvents. Moreover, the structural degradation observed in XRD for high-temperature $N_2$-activated samples ($MOF_{L0}$ at 400° C.) is consistent with their low activity and slight deactivation during dimerization, as these conditions lead to the partial loss of porosity and thereby the intrapore liquid-filling (as seen for $MOF_{L50}$).

Figure 4B:
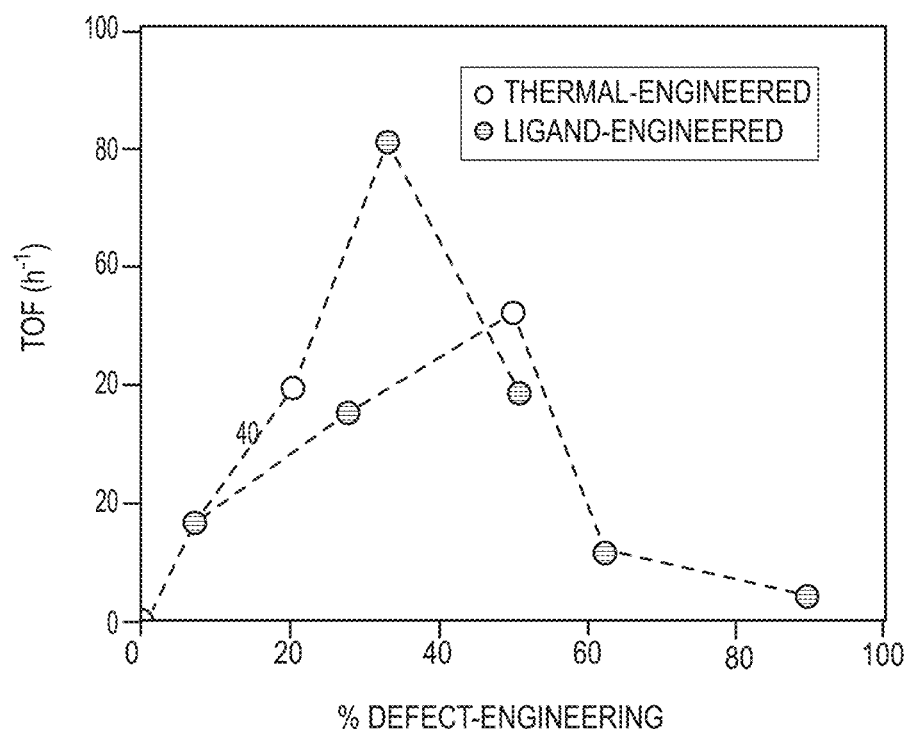
FIG. 4B is a graph showing the Turnover Frequencies per Ru atom as a function of measured defect sites (as quantified from TGA analysis) as described in Example 2. Squared dots in b are shown for long term stability test in (a).

FIG. 4B shows ethylene dimerization turnover frequencies (TOF, per Ru atom) as a function of measured defect content for ligand-engineered ($H_2$-activation at 150° C.) versus MOF catalysts with thermal-engineered defects ($N_2$-activation at 300° C.). Squared dots in FIG. 4B are shown for long term stability tests in FIG. 4A. An evident maximum TOF value is observed for both procedures, related to the highest available Ru—H species, as determined by comparing the CO-DRIFT spectra (FIG. 3B). Measured defect contents above 40% show a decline in dimerization reactivity as a consequence of the structural collapse and the consequent single Ru aggregation created by the excessive deficiency of carboxylates linking the metal-organic crystalline structure in MOFs.

Numerous modifications and variations of the present disclosure are possible in view of the above teachings. It is understood that within the scope of the appended claims, the disclosure may be practiced otherwise than as specifically described herein.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

The invention claimed is:

1. A catalytic reaction process comprising
providing a reactor comprising a microporous catalyst having a defined pore size distribution with a pore diameter ≤2 nm, thereby allowing a controlled pore-filling, wherein the reactor operates at a temperature in a range of about −30° C. to about 100° C. and at a pressure in a range of about 0.1 MPa and about 10 MPa,
heating the microporous catalyst in an inert gas atmosphere at a temperature between about 150° C. and about 900° C., wherein the microporous catalyst comprises a carboxylate-based metal-organic framework (MOF) catalyst,
introducing one or more gas-phase reactants into the reactor,
adjusting the temperature and/or the pressure of the reactor such that one or more of the gas-phase reactants condense to form a liquid phase fraction within the micropores of the catalyst, wherein the liquid phase fraction in the micropores is controlled to achieve a mixed liquid/gas phase within the micropores such that the catalytic reaction takes place in a liquid phase.

2. The process of claim 1, wherein in the inert gas comprises $N_2$.

3. The process of claim 1, wherein the catalytic reaction comprises C—C coupling reactions or chain-growth reactions, ethylene epoxidation, ethylene hydrochlorination, CO hydrogenation reactions, or $CO_2$ hydrogenation reactions.

4. A process for converting ethylene into its associated oligomer, the process comprising
providing a reactor comprising a microporous catalyst having a pore size ≤2 nm, wherein the reactor operates at a temperature between about −30° C. and about 200° C. and at a pressure between about 0.1 MPa and about 10 MPa
heating the microporous catalyst in an inert gas atmosphere at a temperature between about 150° C. and about 900° C., wherein the microporous catalyst comprises a metal-organic framework (MOF) catalyst,
introducing a gas-phase ethylene reactant into the reactor, and
adjusting the temperature and/or the pressure of the reactor such that at least a portion of the gas-phase ethylene reactant condenses within the micropores of the catalyst thereby causing the catalytic reaction to take place in a liquid phase.

5. The process of claim 4, wherein the microporous catalyst comprises a carboxylate-based MOF catalyst.

6. The process of claim 5, wherein in the inert gas comprises $N_2$.

7. The process of claim 4, wherein the catalyst includes a Ruthenium (RU) based MOF.

8. A process for converting a $C_2$-$C_4$ alkene into its associated oligomer, the process comprising
providing a reactor comprising a microporous catalyst having a pore size <2 nm, wherein the reactor operates at a temperature between about −30° C. and about 200° C. and at a pressure between about 0.1 MPa and about 10 MPa,
heating the microporous catalyst in an inert gas atmosphere at a temperature between about 150° C. and about 900° C., wherein the microporous catalyst comprises a carboxylate-based metal-organic framework (MOF) catalyst,
introducing a gas-phase $C_2$-$C_4$ alkene reactant into the reactor, and
adjusting the temperature and/or the pressure of the reactor such that at least a portion of the gas-phase $C_2$-$C_4$ alkene reactant condenses within the micropores of the catalyst thereby causing the catalytic reaction to take place in a liquid phase.

9. The process of claim 8, wherein in the inert gas comprises $N_2$.

10. The process of claim 8, wherein the microporous catalyst comprises a metal organic framework (MOF), zeolites, zeotypes, covalent organic frameworks (COF), porous organic polymers, porous molecular solids, porous carbons, or other porous catalysts containing silica, organosilica, silicoaluminate, aluminophosphate, titania, zirconia, and/or ceria.

11. The process of claim 10, wherein the MOF catalyst comprises metals from alkali metals, alkali earth metals, transition metals, rare earth metals or other metals.

12. The process of claim 10, wherein the MOF catalyst comprises Mg, V, Cr, Mo, Zr, Hf, La, Zr, Mn, Fe, Co, Cu, Ni, Zn, Ru, Al, Ga, or mixtures thereof.

13. The process of claim 8, wherein the $C_2$-$C_4$ alkene comprises ethylene.

14. The process of claim 8, wherein the reactor operates at a temperature between about 0° C. and 100° C.

15. The process of claim 8, wherein the reactor operates at a pressure between about 3.0 MPa and 4.5 MPa.

16. The process of claim 8, wherein the reactor operates at a pressure between about 3.5 MPa and 4.5 MPa.

17. The process of claim 8, wherein the $C_2$-$C_4$ alkene has a saturation pressure Psat at the operating temperature, and wherein the reactor is operated at a pressure P such that a relative saturation pressure for the reactor is $P/P_{sat}$ is >0.4.

18. The process of claim 7, wherein the reactor operates at a temperature between about 0° C. and about 60° C. and at a pressure between about 3.3 MPa and about 4.2 MPa.

19. The process of claim 7, wherein after heating the RU-based MOF, the RU based MOF includes at least one catalytically active open metal site.

20. The process of claim 7, wherein the inert gas includes nitrogen, wherein the temperature is between 200° C.-300° C., wherein the RU-based MOF includes at least one catalytically active open metal site after being heated.

* * * * *